United States Patent [19]

Nyui

[11] Patent Number: 4,810,084
[45] Date of Patent: Mar. 7, 1989

[54] RETINAL CAMERA

[75] Inventor: Masaru Nyui, Tokyo, Japan

[73] Assignee: Tokyo Kogaku Kikai Kabushiki Kaisha, Tokyo, Japan

[21] Appl. No.: 893,713

[22] Filed: Aug. 6, 1986

[30] Foreign Application Priority Data

Aug. 12, 1985 [JP] Japan .................................. 60-177190

[51] Int. Cl.$^4$ ................................................ A61B 3/14
[52] U.S. Cl. ..................................... 351/206; 351/213
[58] Field of Search ........................ 351/206, 207, 213

[56] References Cited

U.S. PATENT DOCUMENTS 4,265,518  5/1985  Matsumura .......................... 351/213
4,439,024  3/1984  Ito ...................................... 351/207

Primary Examiner—Rodney B. Bovernick
Assistant Examiner—P. M. Dzierzynski
Attorney, Agent, or Firm—Finnegan, Henderson, Farabow, Garrett & Dunner

[57] ABSTRACT

A retinal camera of the present invention has an illumination optical system for projecting an illumination light to a retina of an eye to be tested and a photographing optical system for photographing a retinal image of the eye to be tested. The illumination optical system is provided in a position substantially conjugate to the retina with a filter member. The filter member is formed as such that transmittance is relatively increased as it goes toward the peripheral portion from the central portion. When the retina of the eye to be tested is illuminated by this illumination optical system, an illumination light quantity per unit area at the peripheral portion side becomes larger than a illumination light quantity per unit area of the central portion side of an illumination light to be formed on the retina. When the retina of the eye to be tested is photographed by such illumination light as mentioned, the retinal image taken is generally uniform in brightness of the central portion and that of the peripheral portion. That is, it can be prevented that the central portion of the retinal image is taken excessive in brightness at the central portion and excessive in darkness at the peripheral portion.

13 Claims, 4 Drawing Sheets

RETINAL CAMERA

FIELD OF THE INVENTION

This invention relates to a retinal camera which can photograph a retinal image having a uniform brightness. In case a retina is photographed by using a retinal camera according to the present invention, a retinal image taken on a retinal photograph is uniform in brightness at its peripheral portion and its central portion.

BACKGROUND OF THE INVENTION

Heretofore, there have been known retinal cameras, wherein an illumination optical system having an illumination light source for illuminating the retina of an eye to be tested is provided with a ring-shaped slit aperture. This ring-shaped slit aperture is disposed to a position substantially conjugate to a pupil of the eye to be tested. This ring-shaped slip aperture is adapted to form a ring-shaped slit illumination light in the vicinity of the pupil. An illumination light emitted from the illumination light source becomes a ring-shaped slit illumination light in the vicinity of the pupil of the eye to be tested, and the retina of the eye to be tested is illuminated by the ring-shaped slit illumination light. The illumination light reflected by the retina of the eye to be tested is guided to a photographing optical system for photographing the retina. The photographing optical system is prevented from entering therein a harmful light reflected by the cornea, anterior face of the crystal, etc. of the eye to be tested, since the retina is illuminated by the ring-shaped slit illumination light.

However, the conventional retinal cameras have presented such inconveniences as that the brightness is decreased at the peripheral portion of a photographing area with respect to the central portion thereof due to relation of an aperture efficiency of the illumination optical system and the photograph optical system (i.e., the aperture efficiency of the illumination optical system and the photographing optical system exerts influence). That is, in case a retina is photographed by using the conventional camera, an image of the retina photographed shows an excessive brightness at the central portion of the retinal image and a comparatively excessive darkness at the peripheral portion thereof. As seen, the conventional retinal cameras presented a problem that it is difficult to obtain a retinal photograph having a uniform brightness all over the photographing area of the retina of the eye to be tested.

Particularly, in recent years, since there is such a tendency as that the photographing angle of view of a retinal camera is widened, the afore-mentioned problem is closed up. That is, it is an important technical problem for a retinal camera of recent years to eliminate irregularity of brightness of a retinal image. To this end, an attempt is being made to correct an illumination light quantity on the retina of an eye to be tested by vignetting, wherein the diameter, position, etc. of a ring-shaped slit aperture provided to an illumination light optical system are altered.

However, the ring-shaped slit aperture provided to the illumination optical system is restricted based on removal of harmful reflection light and possible pupil diameter. Because of the foregoing, there is a limitation in correcting the image light quantity ratio per unit area of the central portion of the retinal image to be photographed and the peripheral portion thereof. Particularly, it becomes more difficult to effect such a correction as mentioned due to the tendency of wider photographing angle of view and photographable smaller pupil diameter.

SUMMARY OF THE INVENTION

The present invention was accomplished in view of the above situation.

It is therefore a first object of the present invention to provide a retinal camera, including a filter member which is larger in transmittance at the peripheral portion than the central portion thereof is positioned substantially conjugate to the retina of an eye to be tested in an illumination optical system for substantially uniformly illuminating the retina by projecting an illumination light to the retina wherein an illumination light quantity per unit area at the peripheral portion is made larger than an illumination light quantity per unit area at the central portion the filter member, so that a retinal image having a uniform brightness can be photographed.

That is, since the retinal camera according to the present invention is provided in a position substantially conjugate to the retina of the eye to be tested in an illumination optical system with a filter member which has increased transmittance from the central portion to the peripheral portion, thereof difference of brightness of the central portion and the peripheral portion produced due to influence of an aperture efficiency is corrected, thereby enabling a photograph of a retinal image having a uniform brightness to be taken.

A second object of the present invention is to provide a retinal camera which is simple in construction even if it is constructed as such that a retinal image having a uniform brightness can be photographed.

A third object of the present invention is to provide a retinal camera, wherein a retinal image having a uniform brightness can be photographed without altering the constitution of a photographing optical system.

BRIEF DESCRIPTION OF THE DRAWINGS

FIGS. 4 and 5 are illustrations showing a first modified embodiment of the filter member of FIG. 1, wherein FIG. 4 is a plan view thereof and FIG. 5 is a side view thereof;

FIGS. 6 and 7 are illustrations showing a second modified embodiment of the filter member shown in FIG. 1, wherein FIG. 6 is a plan view thereof and FIG. 7 is a sectional view taken on line VII—VII of FIG. 6; and FIGS. 8 and 9 are illustrations showing a second embodiment of a retinal camera according to the present invention, wherein FIG. 8 is an illustration of an optical system path thereof and FIG. 9 is a plan view of a rotary plate shown in FIG. 8.

DESCRIPTION OF THE PREFERRED EMBODIMENTS

Figure 1:
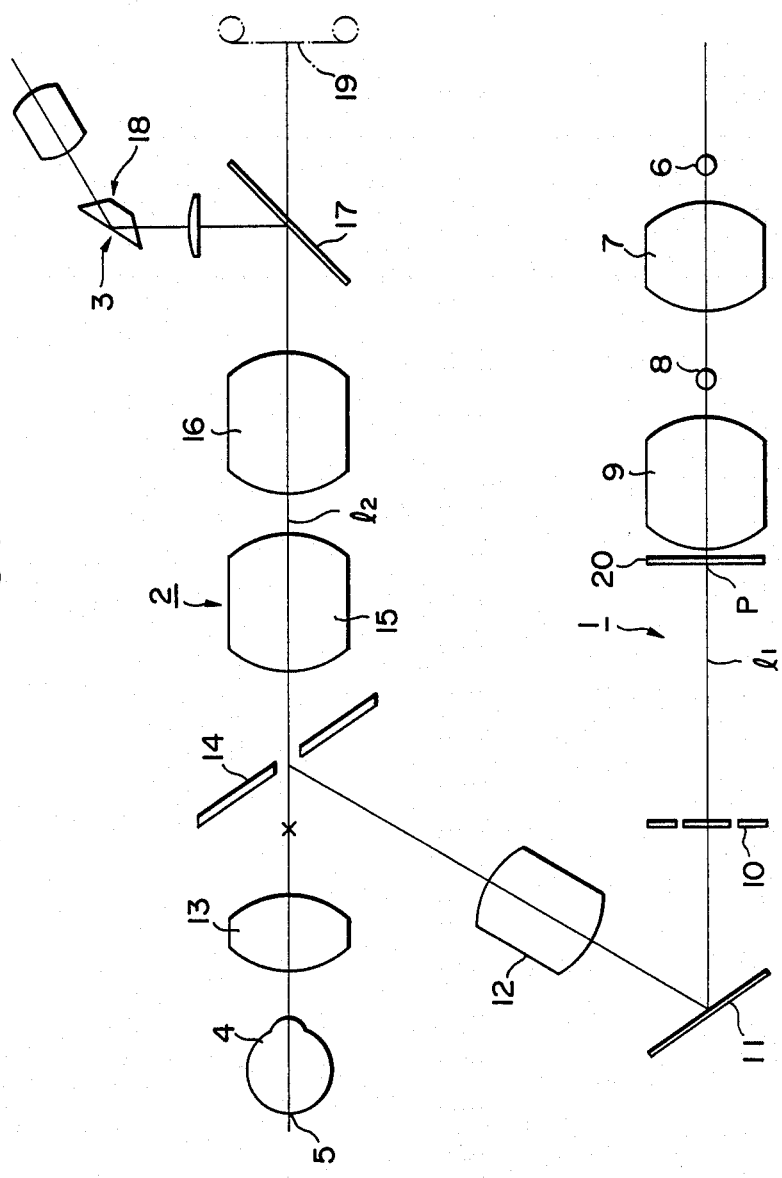
FIG. 1 is an illustration of an optical system path showing a first embodiment of a retinal camera according to the present invention.

In FIG. 1, reference numeral 1 denotes an illumination optical system, 2 denotes a photographing optical system, 3 denotes a finder optical system, 4 denotes an eye to be tested and 5 denotes a retina of the eye 4. The illumination light system 1 generally comprises an observation light source 6, a first condenser lens 7, a photographing light source 8, a second condenser lens 9, a ring-shaped slit aperture 10, a mirror 11, and a relay lens 12. Reference symbol $l_1$ denotes an optical axis of the illumination light system 1. The ring shaped slit aperture 10 is disposed to a position substantially conjugate to the pupil of the eye 4.

The photographing optical system 2 generally comprises an objective lens 13, a mirror with opening 14, a focussing lens 15, and an imaging lens 16. Reference symbol $l_2$ denotes an optical axis of the photographing optical system 2. The finder optical system 3 generally comprises a quick return mirror 17 and a lens system 18. The quick return mirror 17 is inserted into an optical path of the photographing optical system when observing. And, the quick return mirror 17 is retreated outside of the optical path when photographing. Reference numeral 19 denotes a film.

The observation light source is lighted up when observing and extinguished when photographing. The photographing light source 8 is extinguished when observing and lighted up when photographing. The first condenser lens 7 has such a function as to condense an illumination light when observing. The second condenser lens 9 has such a function as to condense an illumination light when photographing. The respective illumination lights when observing and photographing are guided to the mirror 11 after passing through the ring-shaped slit aperture 10 and projected to the retina 5 of the eye 4 through the relay lens 12, the mirror with opening 14 and the objective lens 13. Hereby, the respective illumination lights become a ring-shaped slit light in the vicinity of the pupil of the eye 4 and are guided to the retina 5.

The illumination light optical system 1 is provided to a substantially conjugate position P to the retina 5 with a filter member 20. The filter member 20 has such a function as to effect a correction in such a manner as to drop illumination light quantity at the central portion and relatively increase illumination light quantity at the peripheral portion to obtain a retinal image having a uniform brightness by taking an influence of an aperture efficiency of the illumination optical system 1 and the photographing optical system 2 into consideration.

Figure 2:
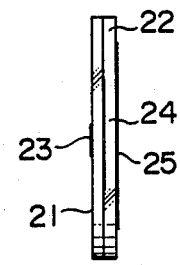
FIG. 2 is an enlarged side view of a filter member shown in FIG. 1.

The filter member 20, as shown in FIG. 2, is formed of two sheets of disc-shaped filters 21 and 22 attached together. One surface of the disc-shaped filter 21 is provided at the central portion with a circular semi-transmitting surface 23 of a small diameter. The other surface of the disk-shaped filter 21 is provided at the central portion with an annular upper half transmitting surface 24 of a medium diameter. One surface of the disc-shaped filter 22 is provided at the central portion with an annular semi-transmitting surface 25 of a large diameter. The annular semi-transmitting surfaces 23, 24 and 25 may be formed by evaporating, for example, a metal film having a semi-transmitting property to each surface of colorless, transparent glass plate.

Figure 3:
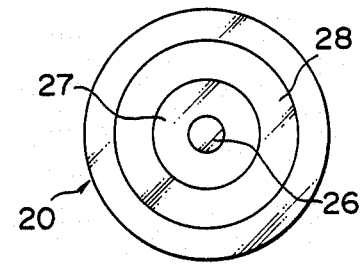
FIG. 3 is a plan view of the filter member of FIG. 2.

The filter member 20, as shown in FIG. 3, is formed with ring belts 26, 27 and 28 which become larger in transmittance as it approaches to the peripheral portion by the annular, semi-transmitting surfaces 23, 24 and 25. An illumination light passed through the condenser lens is more largely absorbed at the central portion than the peripheral portion by the ring belts 26, 27 and 28. Since the filter member 20 is disposed to a position substantially conjugate to the retina 5, light quantity distribution of an illumination light formed on the retina 5 corresponds to transmittance distribution of the filter member 20. Accordingly, the transmittance distribution of the filter member 20 is set in such a manner as to correct irregularity of brightness of a retinal image to be photographed.

Figure 4:
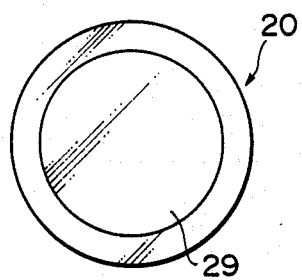
Figure 5:
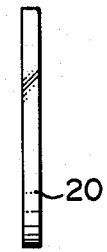

FIGS. 4 and 5 illustrate a first modified embodiment of the filter member 20. The filter member 20 is formed with an annular semi-transmitting surface 29 which is continuously increased in transmittance as it approaches to the peripheral portion from the central portion by vacuum deposition.

Figure 6:
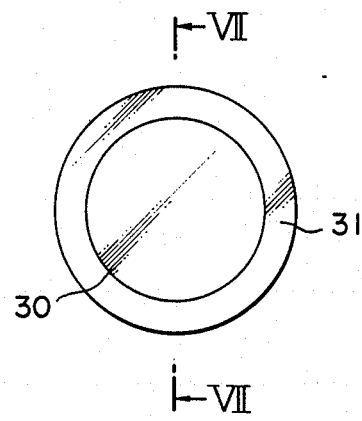
Figure 7:
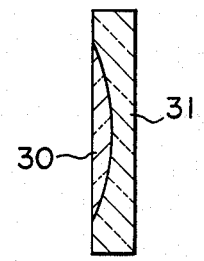

FIGS. 6 and 7 illustrate a second modified embodiment of the filter member 20. This filter member 20 is formed by attaching a filter 30 formed of a convex surface-shaped semi-transmitting material and a concave surface-shaped filter 31 having a concave surface corresponding to the convex surface of the convex surface-shaped filter 30. The filter members 30 and 31 each continuously changed in thickness from the peripheral portion to the central portions thereof due to the curvature of the surface of each. As a result, transmittance of the filter member 20 is continuously increased from the central portion to the peripheral portion.

Figure 9:
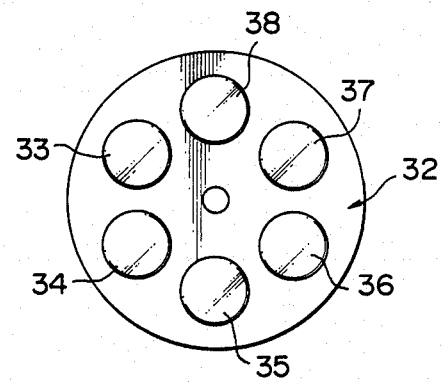
Figure 8:
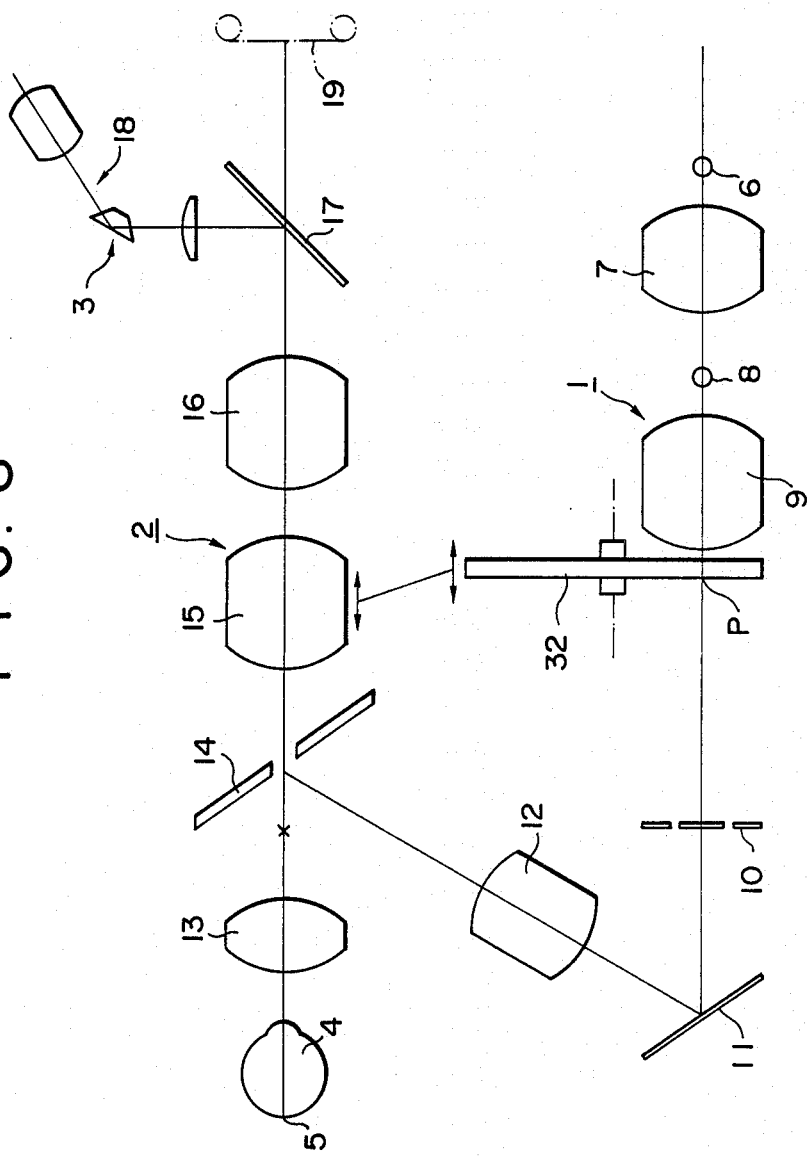

FIGS. 8 and 9 illustrate a second embodiment of a retinal camera according to the present invention. In this second embodiment, in view of the fact that a pupil diameter, etc. are different per every eye to be tested depending on whether the diopter of the eye to be tested is at the plus side or the minus side, a filter member 20 suitable to the eye to be tested is selectively inserted into the illumination optical system 1. In this embodiment, a rotary plate 32 is provided with a plurality of disc-shaped filter members 33, 34, 35, 36, 37 and 38. To position a respective disc-shaped filter member in conjugate relation with the retina 5 of the eye 4 in accordance with the diopter power of the eye 4, the rotary plate 32 is moved in the direction of the optical axis $l_1$ of the illumination optical system 2 in association with the movement of the focussing lens 15.

Additional advantages and modifications of the present invention will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A retinal camera, comprising:
   an illumination optical means for projecting an illumination light to a retina of an eye being examined;
   a photographing optical means for photographing a retinal image of the eye being tested;
   filter means, disposed at a position substantially conjugate to the retina of the eye being examined in said illumination optical means, for substantially uniformly illuminating the retina;
   said filter means including at least one filter member having a disc-shaped transmitting base plate, a first circular semi-transmitting surface having a first diameter centrally attached to a surface of said base plate, and a second circular semi-transmitting surface having a second diameter, larger than said first diameter, centrally attached to a surface of said base plate such that ring bands having different respective transmittances are formed by overlapping said first and second semi-transmitting surfaces along the optical axis of said illumination optical means.

2. A retinal camera according to claim 1, wherein a colorless transparent glass plate is used as said disk-shaped transmitting base plate, and said first and second circular semi-transmitting surfaces are formed by evaporating a semi-transmitting metal film onto a surface of said glass plate.

3. A retinal camera according to claim 1, wherein said filter means comprises a plurality of filter members selectively insertable into said illumination optical system.

4. The retinal camera of claim 3, wherein said filter means includes a plurality of concentric ring bands each having a predetermined transmittance, said transmittances being increased from the central portion to the peripheral portion of said filter such that the difference in brightness between the illumination light passed through the central portion of said filter means and the illumination light passed through the peripheral portion of said filter means is reduced.

5. A retinal camera according to claim 1, wherein said filter means is movable in association with a focussing lens provided in said photographing optical system.

6. A retinal camera according to claim 1, wherein said illumination optical system includes a condenser lens and a ring-shaped slit aperture, and said filter means being positioned between said condenser lens and said ring-shaped slit aperture.

7. A retinal camera, comprising:
illumination optical means for projecting an illumination light to a retina of an eye to be tested;
photographing optical means for photographing a retinal image of the eye to be tested;
filter means for substantially uniformly illuminating the retina, said filter means including at least one filter member configured such that transmittance of illumination light passing therethrough is continuously increased from the central portion to the peripheral portion of said filter member;
said filter member being disposed at a position substantially conjugate to the retina of the eye to be tested in the illumination optical system such that the difference in brightness between illumination light passed through the central portion and illumination light passed through the peripheral portion of said filter member when impinging on the retina is reduced.

8. A retinal camera according to claim 7, wherein said filter member is formed by evaporating a metal film onto a transparent glass plate under vacuum.

9. A retinal camera according to claim 7, wherein said filter means comprises a plurality of filter members selectively insertable into said illumination optical system.

10. A retinal camera according to claim 7, wherein said filter means is movable in association with a focussing lens provided in said photographing optical system.

11. A retinal camera, comprising:
illumination optical means for projecting an illumination light to a retina of an eye to be tested;
photographing optical means for photographing a retinal image of the eye to be tested;
filter means for substantially uniformly illuminating the retina, said filter means including at least one filter member, disposed conjugate to the retina in said illumination optical means, configured such that transmittance of illumination light passing therethrough is continuously increased from the central portion to the peripheral portion of said filter member;
said filter member having a first disk-shaped semi-transmitting base plate having a concave surface, and a second disk-shaped semi-transmitting base plate having a convex surface configured to mate with said concave surface such that the difference in brightness between illumination light passed through the central portion and the peripheral portion of said filter member when impinging on the retina is reduced.

12. A retinal camera according to claim 11, wherein said filter means comprises a plurality of filter members selectively insertable into said illumination optical system.

13. A retinal camera according to claim 11, wherein said filter means is movable in association with a focussing lens provided in said photographing optical system.

* * * * *